(12) United States Patent
Brown

(10) Patent No.: US 8,370,177 B2
(45) Date of Patent: Feb. 5, 2013

(54) PERSONALIZED BODY IMAGE

(75) Inventor: Stephen J. Brown, Woodside, CA (US)

(73) Assignee: Robert Bosch Healthcare Systems, Inc., Palo Alto, CA (US)

(*) Notice: Subject to any disclaimer, the term of this patent is extended or adjusted under 35 U.S.C. 154(b) by 0 days.

(21) Appl. No.: 13/043,961

(22) Filed: Mar. 9, 2011

(65) Prior Publication Data

US 2011/0246233 A1    Oct. 6, 2011

Related U.S. Application Data

(63) Continuation of application No. 12/608,110, filed on Oct. 29, 2009, now Pat. No. 7,925,522, which is a continuation of application No. 11/610,044, filed on Dec. 13, 2006, now Pat. No. 7,613,621, which is a continuation of application No. 10/755,037, filed on Jan. 9, 2004, now Pat. No. 7,555,436, which is a continuation of application No. 09/761,337, filed on Jan. 16, 2001, now abandoned, which is a continuation of application No. 09/441,408, filed on Nov. 16, 1999, now abandoned, which is a continuation of application No. 08/784,740, filed on Jan. 16, 1997, now Pat. No. 6,032,119.

(51) Int. Cl.
*G06Q 50/00*    (2012.01)

(52) U.S. Cl. .......................................... 705/3; 600/300

(58) Field of Classification Search ................. 705/2–4; 600/300

See application file for complete search history.

(56) References Cited

U.S. PATENT DOCUMENTS

| | | | | |
|---|---|---|---|---|
| 4,803,625 A | * | 2/1989 | Fu et al. ........................ | 600/483 |
| 4,839,822 A | * | 6/1989 | Dormond et al. ............... | 706/45 |
| 5,075,675 A | * | 12/1991 | Barker et al. ................. | 715/794 |
| 5,704,366 A | * | 1/1998 | Tacklind et al. ............... | 600/529 |
| 5,867,821 A | * | 2/1999 | Ballantyne et al. ............... | 705/2 |

* cited by examiner

*Primary Examiner* — Sind Phongsvirajati
(74) *Attorney, Agent, or Firm* — Christopher P. Maiorana, PC

(57) ABSTRACT

Delivery of health information to a patient suffering from a chronic condition is personalized by displaying the health information directly on a customized image of a body. The patient's medical record, standards of care for the condition, prescribed treatments, and patient input are applied to a generalized health model of a disease to generate a personalized health model of the patient. The personalized health model comprises an HTML file encoding an image map of a body. The body image illustrates the health condition of the individual patient. Preferably, data is collected from health provider sources and stored in a database on a server at a service provider site. The data is processed at the server, and is displayed in the patient's home using a TV connected to a multimedia processor. The multimedia processor connects the television set to a communications network such as the Internet. Applications include preventive care of chronic diseases such as diabetes and asthma.

19 Claims, 8 Drawing Sheets

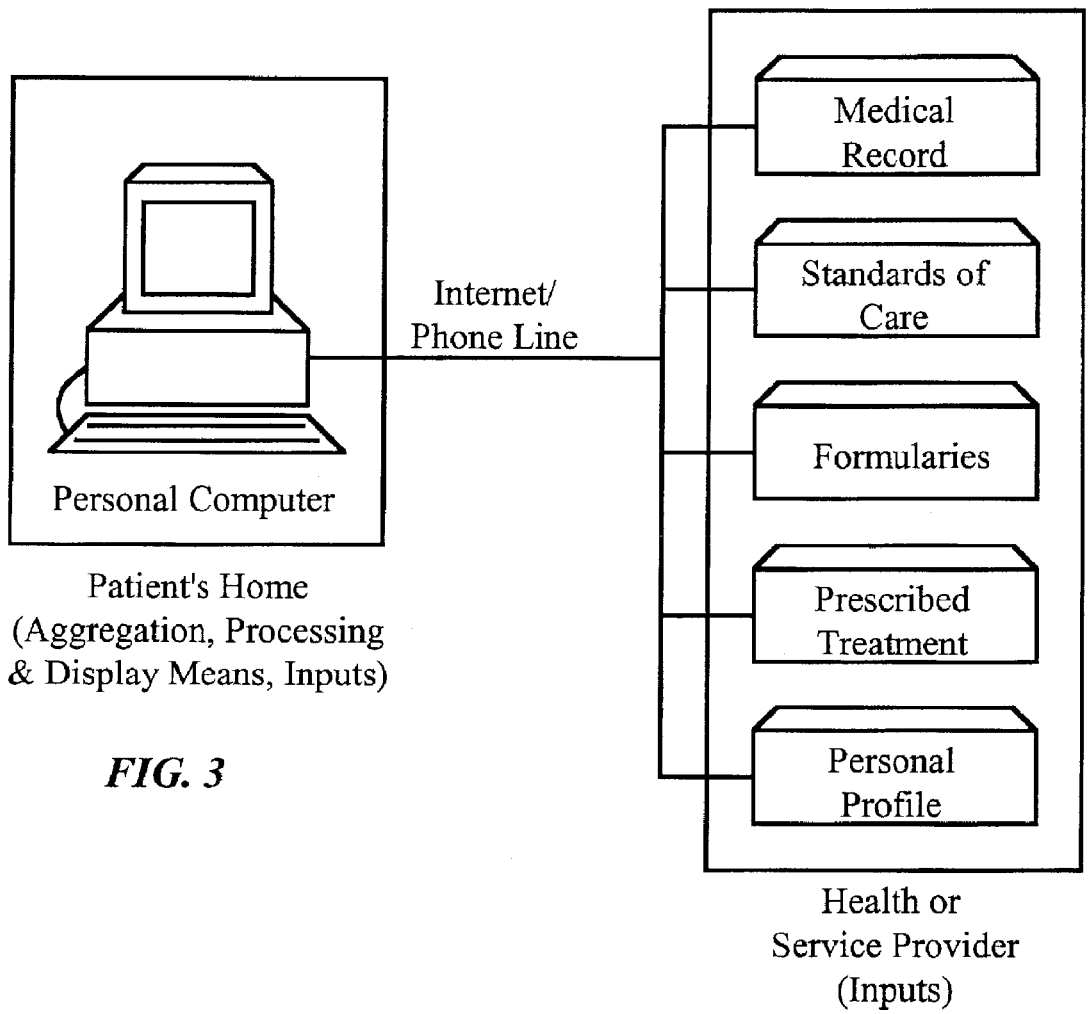
*FIG. 3*
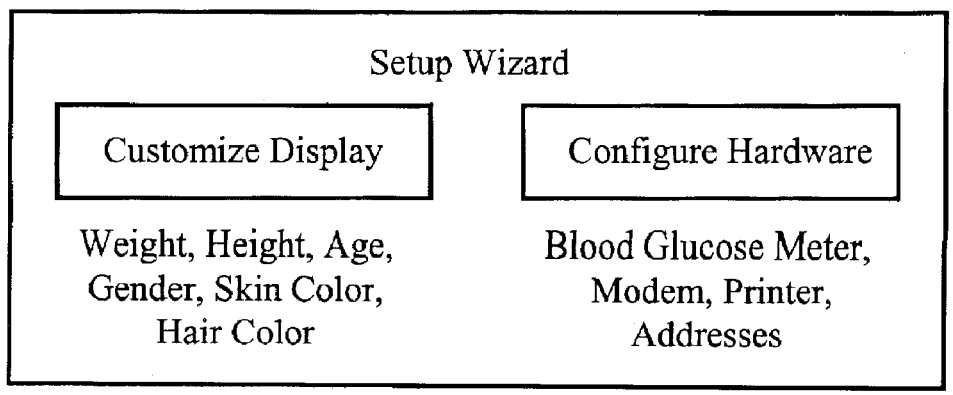
*FIG. 4-A*

*FIG. 4-B* 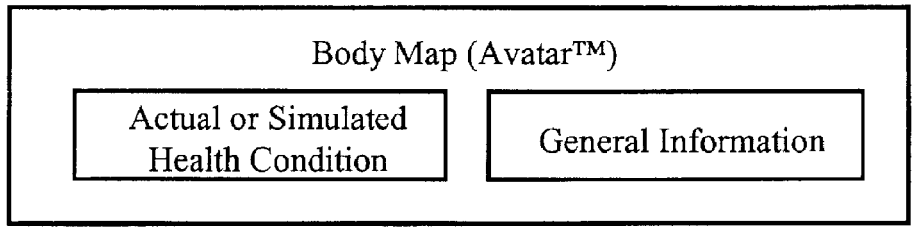
*FIG. 4-C* 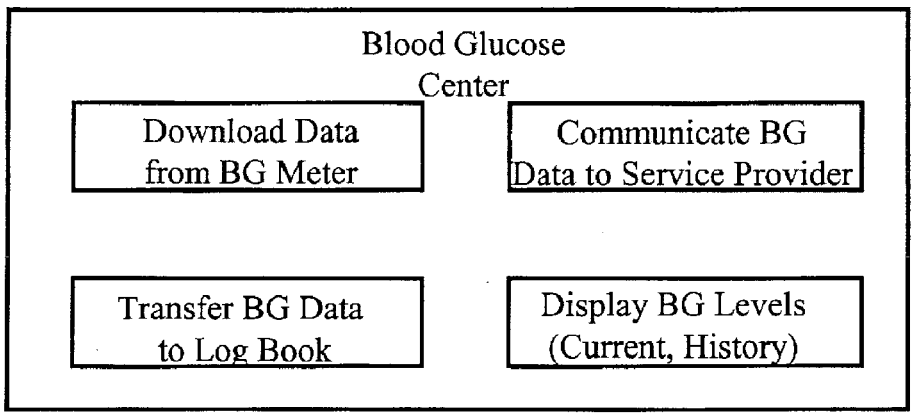
*FIG. 4-D* 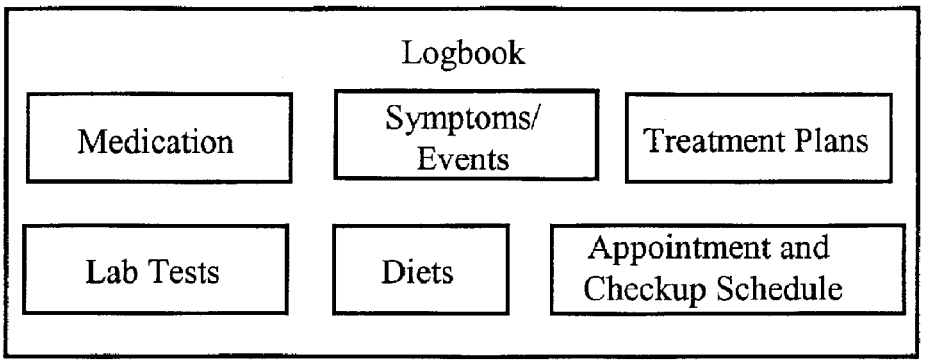
*FIG. 4-E* 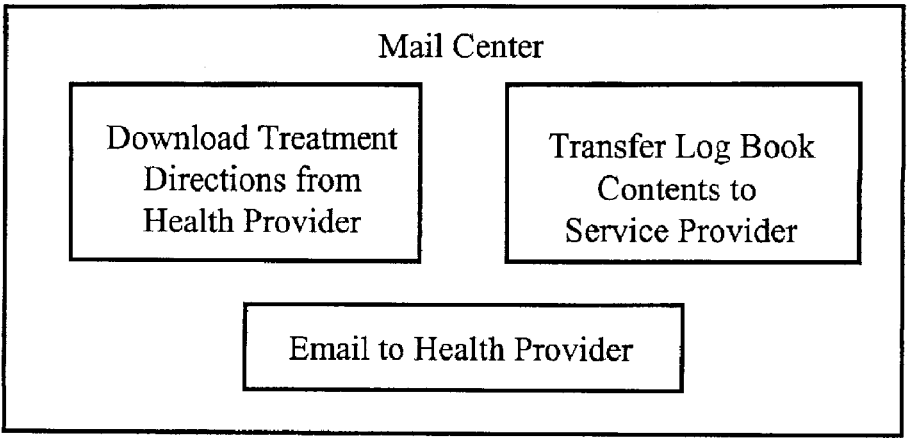

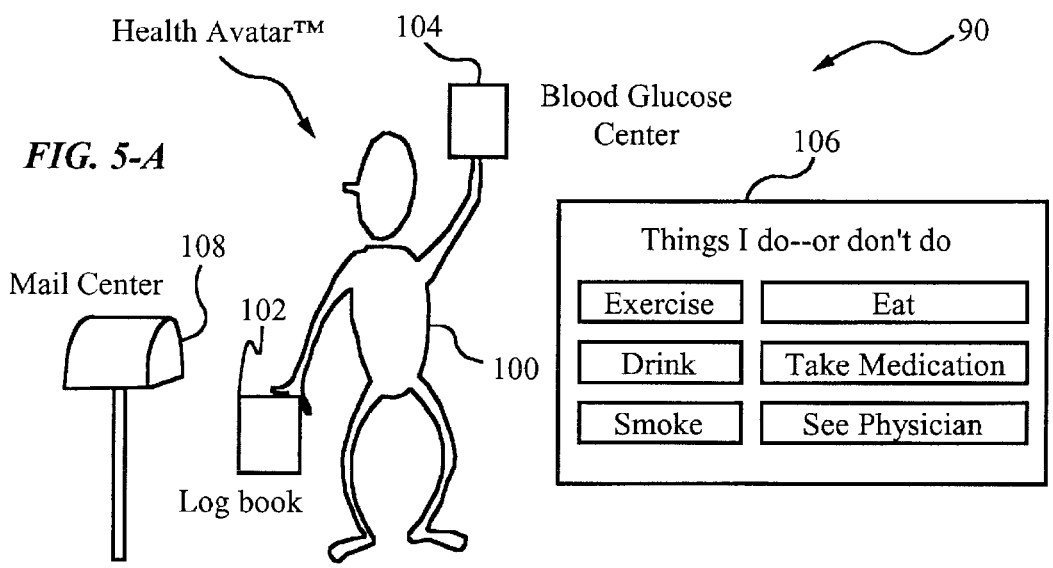
*FIG. 5-A*
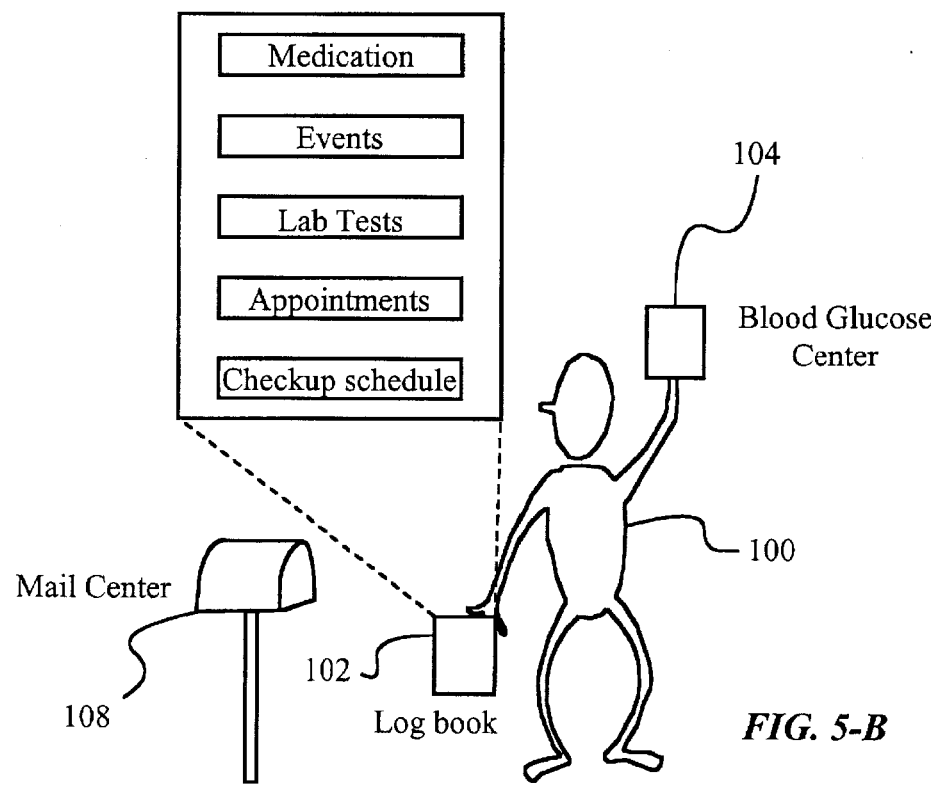
*FIG. 5-B*

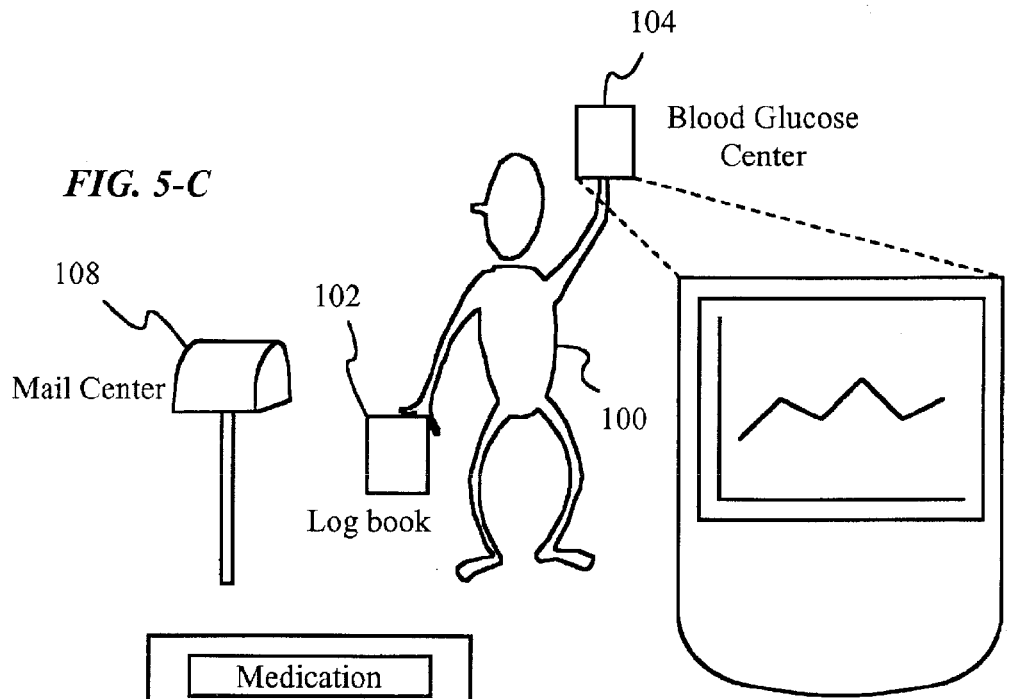
FIG. 5-C
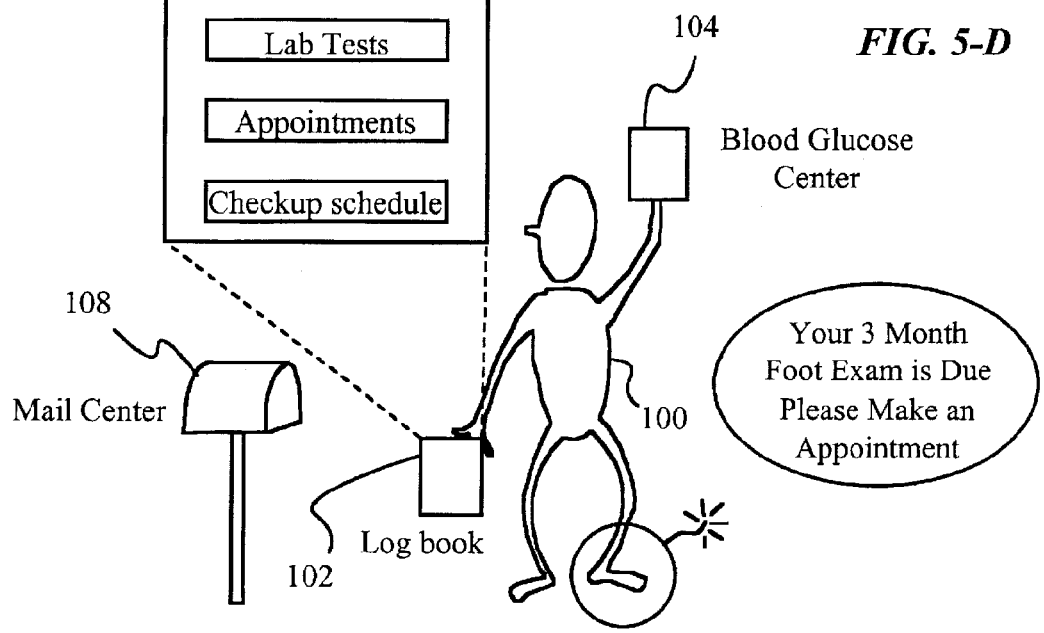
FIG. 5-D

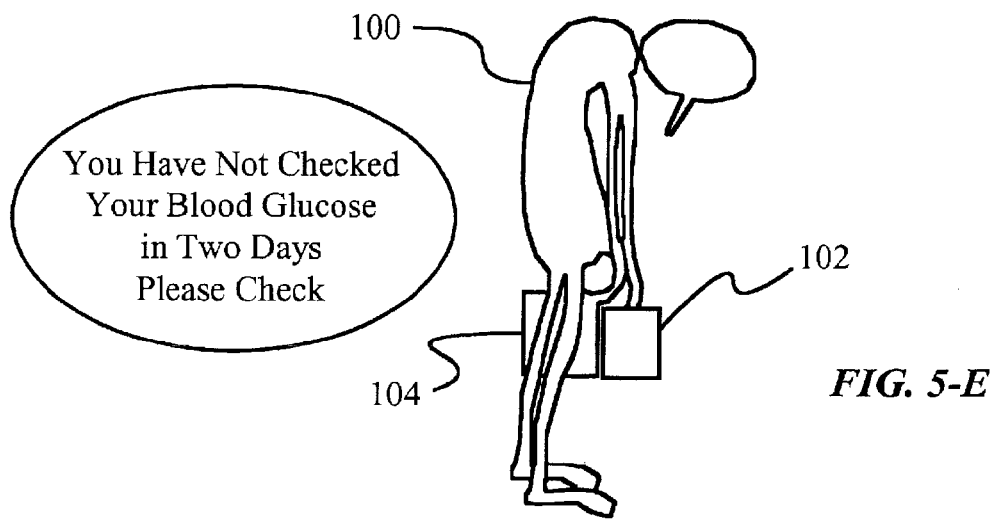
*FIG. 5-E*
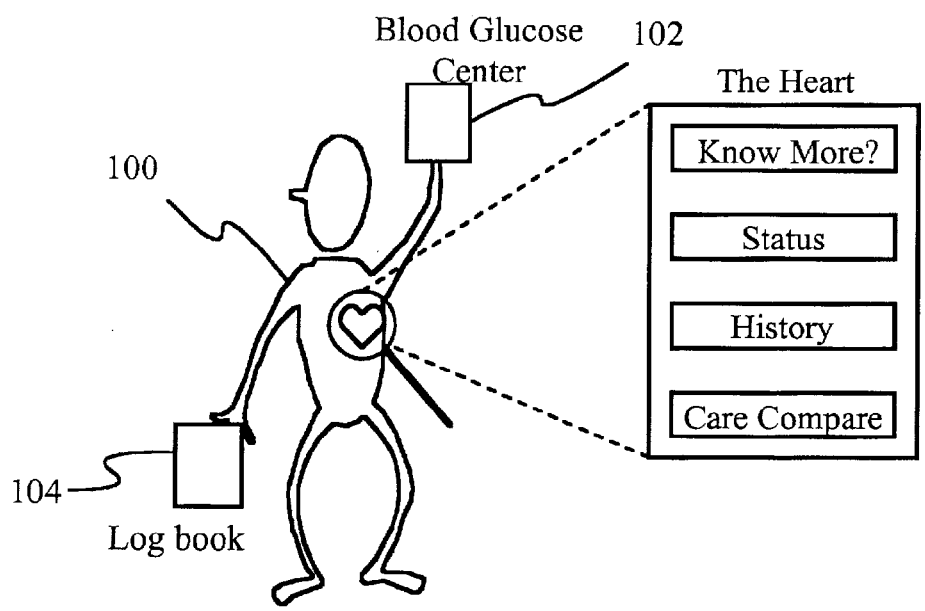
*FIG. 5-F*

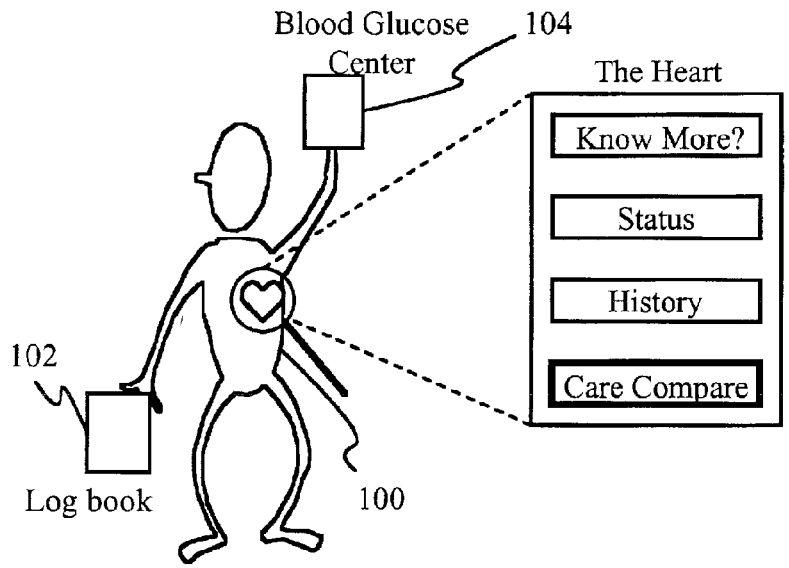

*FIG. 5-G*

You have searched the database for TESTS done in relation to DIABETES and HEART

1. Heart Exam
43% of people with Diabetes had no heart exam performed in one year.

57% of people with Diabetes had at least one heart exam performed in one year.

More Information?
Press Here for detailed info about the test, including the ADA's recommendations for tests in people with diabetes.

PERSONALIZED BODY IMAGE

CONTINUATION APPLICATION DATA

This application is a continuation of U.S. Ser. No. 12/608,110, filed Oct. 29, 2009, now U.S. Pat. No. 7,925,522 which is a continuation of U.S. Ser. No. 11/610,044, filed Dec. 13, 2006, now U.S. Pat. No. 7,613,621 which is a continuation of U.S. Ser. No. 10/755,037, filed Jan. 9, 2004, now U.S. Pat. No. 7,555,436 which is a continuation of U.S. Ser. No. 09/761,337, filed Jan. 16, 2001, now abandoned, which is a continuation of U.S. Ser. No. 09/441,408, filed Nov. 16, 1999, now abandoned, which is a continuation of U.S. Ser. No. 08/784,740, filed Jan. 16, 1997, now U.S. Pat. No. 6,032,119, issued Feb. 29, 2000, each of which are incorporated by reference.

FIELD OF THE INVENTION

This invention relates to computer systems for managing health care, and in particular to a system and method for displaying personalized health information to a patient having a chronic disease or health condition.

BACKGROUND OF THE INVENTION

The health care community has recognized in recent years the importance of prevention care in managing patients' health. Preventive care is particularly important in managing the health of patients having chronic diseases or long-term conditions. Preventive care includes educating patients about their disease, ensuring communication between patients and health care providers (e.g., doctors), and providing patients with tools and/or treatments for managing their disease.

Commonly used preventive care approaches suffer from several drawbacks. Much of health care is voluntary, and thus a large fraction of health care resources is typically spent on patients who are actively seek involvement in their care. A large number of patients do not actively seek information and treatment in the absence of symptoms, however. Also, health providers receive very little information on whether patients are complying with preventive care guidelines. Thus, health providers often are not able to take remedial steps before the disease affects the patients symptomatically (e.g., through pain). Reaching passive patients is thus critical to delivering effective preventive care.

The mass-marketing techniques used for health education by most health maintenance organizations (HMOs) and insurance companies allow little customization of information to an individual patient's needs. Consequently, many patients may not directly identify with the educational approaches used by their health providers. Personalizing health education would significantly raise the effectiveness of preventive care, especially in children and adolescents.

U.S. Pat. No. 5,549,117 describes a system for communicating health information between health providers and patients having a chronic disease such as asthma. A patient unit displays health information, and communicates health information between the patient and a health provider. The display is relatively impersonal, however.

OBJECTS AND ADVANTAGES OF THE INVENTION

It is a primary object of the present invention to provide a personalized display of a health condition of a patient, such that the patient identifies with the display. It is another object of this invention to provide a method of motivating a patient to follow a prescribed treatment regimen. It is yet another object of this invention to provide a health data display that can be easily comprehended. It is still another object of this invention to provide a system and method for involving patients in their own care, for providing feedback to patients about their health condition, and for monitoring patients' progress in managing their health condition.

SUMMARY OF THE INVENTION

A system of the present invention comprises a set of inputs, a processing means in communication with the inputs, and a display means in communication with the processing means. The set of inputs generate a set of data $\{D[j]\}$, $j=1 \ldots J$. A datum $D[j]$ of the set $\{D[j]\}$ characterizes a personal health condition of a patient. The processing means generates a personalized health model of the patient from a generalized health model of the patient and from the data set $\{D[j]\}$. The display means generates a display comprising a body image. The body image illustrates the personalized health model.

The personalized health model is a parameterized model of the health of the individual patient under treatment. The personalized health model is defined by a set of parameters $\{P[k]\}$, $k=1 \ldots K$. The generalized health model is a model of the disease or condition under treatment. The generalized health model is defined by a set of functions $\{f[k]\}$ that specify the dependence of $\{P[k]\}$ on $\{D[j]\}$. That is, $P[k]=f[k](\{D[j]\})$ for all k. The processing means assigns values to the parameters $\{P[k]\}$ using the data $\{D[j]\}$. Parameters suitable for characterizing various diseases include condition of a body part/organ, blood glucose level, respiratory flow, blood pressure, cholesterol level, patient weight, T-cell count, and frequency of health episodes.

The set of inputs comprises a medical record of the patient, as well as records of: a standard of care for the general health condition or disease of the patient, a prescribed treatment of the patient, a display preference, a personal profile of the patient. The set of inputs further comprises a patient identification means (preferably a card) connected to the display means. The patient identification means specifies the identity of the patient corresponding to a particular display. The patient identification means also specifies a prescribed treatment of the patient and an address of the processing means, allowing a communication between the display means and the processing means. The set of inputs also comprises a patient feedback means (preferably a keyboard) in communication with the processing means, for allowing the patient to communicate a subset of feedback data to the processing means. The feedback means also allows the patient to enter a subset of simulation data characterizing a simulated personal health condition of the patient.

The display means preferably comprises a television set, and a multimedia processor for connecting the television set to the processing means. The display comprises a section assigned to a parameter $P[k]$. In particular, the body image comprises a section assigned to a parameter $P[k]$. A set of characteristics of the body image match a set of predetermined physical characteristics, such that the patient is able to customize the appearance of the body image. Such physical characteristics include age, height, gender, weight, skin color, and hair color. In a particular embodiment, the body image comprises a reproduction of an image of the patient (e.g., a photograph of the patient). In another embodiment, the body image comprises an image of a fictional character.

Preferably, the processing means is in communication with the display means over a remote network, such that the processing means is able to handle processing for multiple display means located at different patient locations. The processing means is in communication with at least some of the inputs over a remote network. Processing means at a service provider location can thus access inputs at a health care provider location. A data aggregation means (preferably a database) is in communication with at least some of the inputs and with the processing means. The data aggregation means collects a subset of the data set {D[j]} from the set of inputs, allowing a reduction in the number of direct connections between the processing means and the inputs. The data aggregation means is in communication with the display means over a remote network, so that the data aggregation means stores data for multiple patients.

DESCRIPTION OF THE FIGURES

FIG. 3 shows an alternative architecture of a system of the present invention.

FIG. 4-A depicts the functions of a setup wizard in an embodiment of the present invention.

FIG. 4-B illustrates the functions of a body image module of the present invention.

FIG. 4-C shows the functions of a blood glucose center module of the present invention.

FIG. 4-D shows the functions of a logbook module of the present invention.

FIG. 4-E shows the functions of a mail center module of the present invention.

FIG. 5-A illustrates schematically an introductory screen shot for a diabetes treatment system of the present invention.

FIG. 5-B illustrates the display resulting from the patient's accessing the log book section of the display of FIG. 5-A.

FIG. 5-C illustrates the display resulting from the patient's accessing a subsection of the blood glucose center section of the display of FIG. 5-A.

FIG. 5-D shows a warning resulting from the patient's failure to have a timely foot checkup, according to the system illustrated in FIG. 5-A.

FIG. 5-E shows a warning resulting from a patient's failure to check a blood glucose level according to the patient's treatment plan, according to the system illustrated in FIG. 5-A.

FIG. 5-F shows the display of the system illustrated in FIG. 5-A following the patient's accessing of a display subsection corresponding to the heart.

FIG. 5-G shows the display of the system illustrated in FIG. 5-F following a patient request for comparative care information on the heart.

DETAILED DESCRIPTION

In the ensuing description, the notation {A[j]} is understood to refer to a set of A[j], for j taking some values between a minimum value 1 and a maximum value J. The notation A[j] is understood to refer to some (fixed) j.

Figure 1:
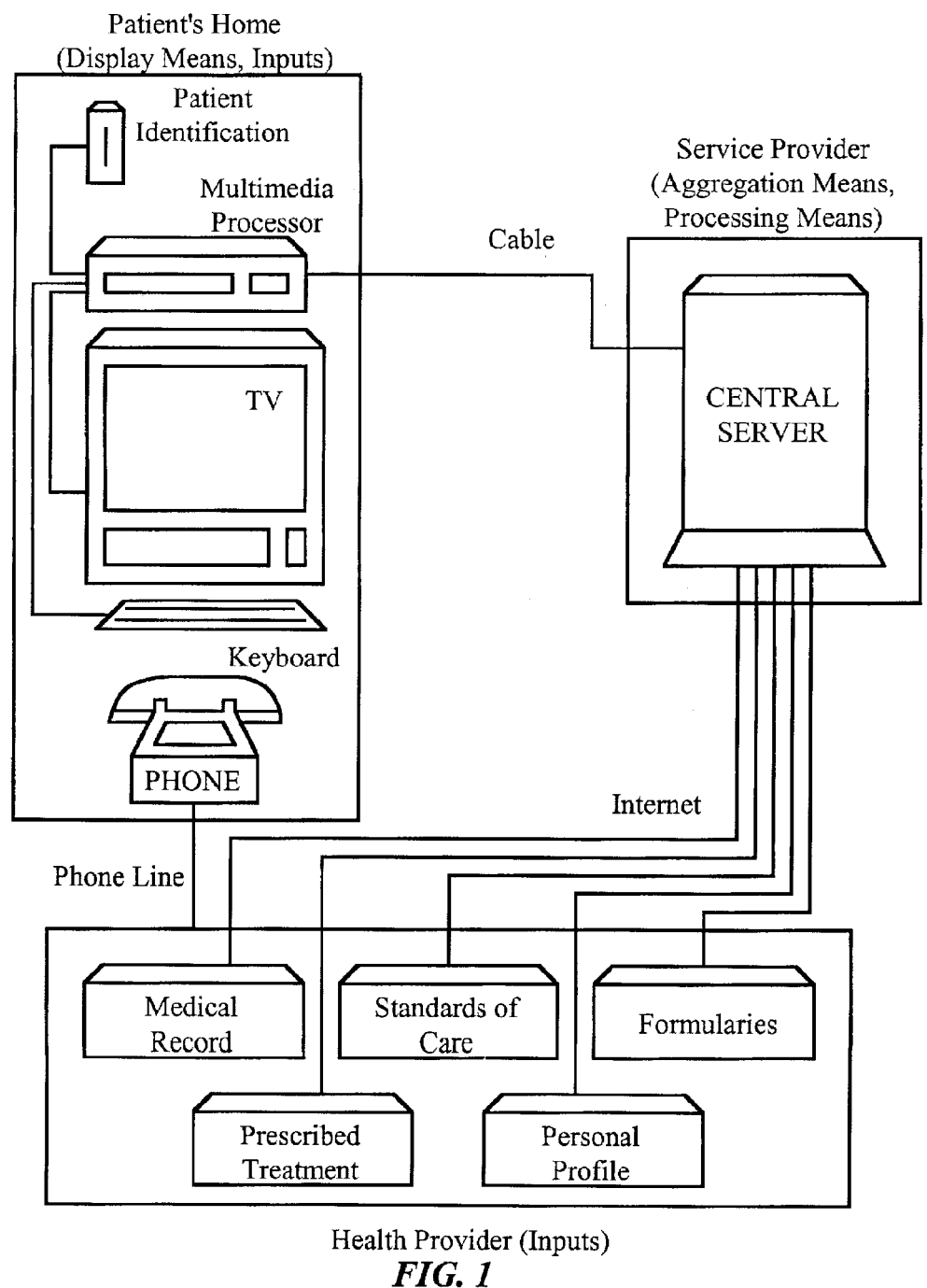
FIG. 1 shows the architecture of a system for health information delivery in a preferred embodiment of the present invention.

FIG. 1 is a schematic diagram illustrating a preferred architecture for a system of the present invention. A processing means (preferably computer software) located on a central server is in communication over remote communication networks with a display means and a set of inputs. The central server processes information for multiple patients, and is thus capable of communicating with multiple display means and input locations. The central server comprises a data aggregation means, preferably a database, in communication with the set of inputs and with the processing means. The data aggregation means collects a subset of the data set {D[j]} from the inputs. Data collected by the data aggregation means is accessed by the processing means. The display means is located at the patient's home. Preferably, the central server is in communication with the health provider over the Internet, and with the patient's home over a cable television delivery line.

The display means preferably comprises a conventional television receiver, and a means for connecting the TV set to a communications network, as illustrated in FIG. 1. Preferably, the TV set is connected to the Internet via a multimedia processor such as a WebTV™ Internet Terminal from WebTV Networks (distributed by Sony). The multimedia processor is in communication over a remote network (such as the Internet, a phone line, or cable used for delivery of cable television programming) with a server at a service provider location.

The multimedia processor connects the processing means on the central server to inputs located at the patient's home: a patient feedback means preferably comprising a keyboard, and a patient identification means preferably comprising a data-bearing card, or "smart card". The multimedia processor has a receiving slot for receiving the patient identification smart card. The patient identification card contains an encrypted patient code, a prescribed treatment for the patient, and a URL address of the processing means. The keyboard allows the patient to provide a subset of feedback data, including display preferences specifying a formatting of the display.

The set of inputs further comprises inputs located at a health care provider location, including records of: a medical history of the patient, a standard of care for a general health condition or disease of the patient, a prescribed treatment for the patient, and a personal profile of the patient. The above-incorporated U.S. patent application Ser. No. 08/732,158 entitled "Multiple Patient Monitoring System for Proactive Health Management" contains further information on data available to the health care provider.

Examples of data specified by the inputs include blood glucose level histories, generally acceptable blood glucose levels, dates of doctor examinations, generally recommended time periods between doctor examinations, ratings of the patient's interest for a cultural subject (e.g., sports, music), and display customization variables entered by the patient.

Figure 2:
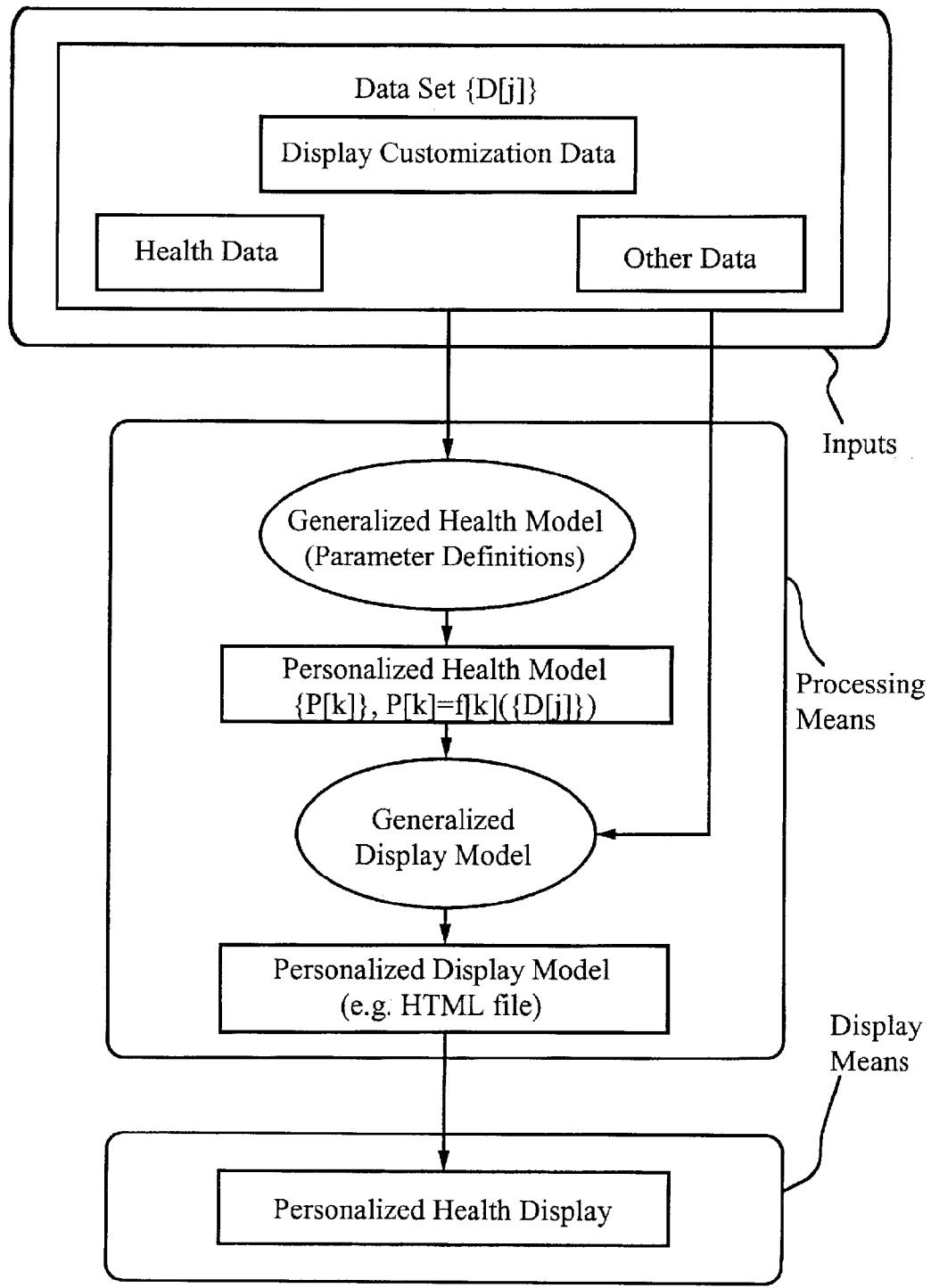
FIG. 2 illustrates processing steps performed on medical and other data to generate a personalized display of the present invention.

FIG. 2 illustrates generally the processing steps performed on the data {D[j]}. A personalized health model of the patient is generated from a generalized health model of the patient's health condition and the patient-specific data {D[j]}. The personalized health model characterizes the patient's current health condition. The personalized health model is defined by a set of parameters {P[k]}, k=1 . . . K. In a preferred embodiment designed for diabetes preventive care, suitable parameters include blood glucose level, conditions of body parts or organs (e.g., heart, feet), and compliance with treatment and/or monitoring protocols. Parameters suitable for the characterization of other diseases include respiratory flow in asthma, blood pressure in hypertension, cholesterol in cardiovascular disease, weight in eating disorders, T-cell or viral count in HIV, and frequency or timing of episodes in mental health disorders.

The generalized health model specifies the dependence of the values {P[k]} on the data {D[j]}. The dependence is determined by a set of functions {f[k]}, where P[k]= f[k]({D[j]}) for all k. That is, the value P[k] of the kth parameter is specified in general by a function f[k]. The function f[k] has as its argument the set of data {D[j]}, i.e. f[k] depends on at least one datum D[j]. The forms of the functions {f[k]} can be readily determined by the skilled artisan according to the disease under treatment.

For example, parameter P[1] may measure the latest recorded blood glucose level of the patient, and the datum D[1] may be the latest blood glucose level recorded in the patient's medical record. Then the function f[1]({D[j]})=D[1], and P[1]=D[1]. Parameter P[2] may measure the health condition of the patient's feet, which may be defined to depend on parameters such as blood glucose level (D[1]), the time between doctor checkups (D[2]), and some other parameter D[j]. Then P[2]=f[2]{D[j]}=f[2](D[1], D[2], D[j]), wherein the exact form of the function f[2] is specified by the generalized health model.

Using the set of parameters {P[k]} and a generalized display model of the patient, the processing means generates a personalized display model of the patient. The personalized display model preferably comprises an HTML file encoding a display comprising a body image. Generating displays using HTML is well known in the art, and will not be discussed here in detail. The formatting of. the body image is preferably customized to the targeted patient, such that the patient identifies with the body image. A set of the characteristics of the body image matches a set of predetermined characteristics. In particular, body image characteristics preferably match physical characteristics chosen by the patient. Such characteristics include age, height, gender, weight and/or build, skin color, hair color, and identity (if any) of a fictional character. In one embodiment, the body image is a schematic figure representing the patient. In other embodiments, the body image is a reproduction (e.g., a photograph) of the patient's appearance, a representation of a cartoon or fictional character, or a representation of a character in a field of interest of the patient (e.g., a favorite basketball player or movie actor).

The body image illustrates the personalized health model of the patient. In particular, the body image comprises sections assigned to body parts/organs of the patient. The image sections graphically represents the health conditions of the corresponding patient parts. Particular characteristics (e.g., color, shape, blinking rate) of the image sections are determined by the set of values {P[k]}. In general, each section of the body is assigned to at least one parameter P[k]. The body image is preferably an image map, such that the patient can access information on a body part or organ by clicking on the corresponding section of the body image.

In an embodiment suitable for the treatment of a diabetes patient, an unacceptable value of a parameter measuring a health condition of the patient's feet leads to a display of swollen feet on the body. The body's feet blink if the time period since the last doctor checkup is longer than a predetermined threshold. In an embodiment suitable for dental hygiene education, the teeth in the body image are represented to be black if a value P[k] measuring a health condition of the patients' teeth is below a predetermined threshold. The appearance of the entire body is used to characterize the personal health condition of the patient. For example, for a patient having low blood glucose levels the corresponding body is displayed to be tired.

In an embodiment used for simulating the effects of hypothetical health decisions or events on the patient's health condition, the data set {D[j]} includes a subset of simulation data characterizing a simulated personal health condition of the patient. The displayed body then contains information on the simulated health condition of the patient. The simulation can be used by the patient to examine, among others, the effects of hypothetical changes in behavior (e.g., diet and sleep patterns) on the patient's health condition.

FIG. 3 shows schematically an alternative system for delivering personalized health information, according to the present invention. A personal computer at the patient's home comprises aggregation, processing and display means. The computer keyboard is an input. Other inputs are at a remote location, and are in communication with the computer over a remote network. An HTML page illustrating the patient's personalized health model is generated on the patient's computer by the processing means.

A particular user interface of a system of the present invention is illustrated in FIGS. 4 and 5. FIGS. 4-A through 4-E illustrate the functions provided by Health Avatar™, a diabetes management application. FIGS. 5-A through 5-G are schematic depictions of screen shots from the same application, illustrating the functions of the application.

As shown in FIG. 4-A, a setup wizard is used by the patient to customize the appearance of the body image, and to enter configuration information for hardware and software in communication with the application. Hardware includes a blood glucose meter, a modem, a printer, while software includes a communications applications for communicating with health and service providers.

The body image itself (the Health Avatar™) displays actual or simulated health information of the patient, according to actual or simulated health data (see FIG. 4-B). The patient can use a blood glucose center (FIG. 4-C) to download information from a blood glucose meter, to transfer blood glucose data to the service provider database, to transfer blood glucose data to a logbook, and to display current blood glucose levels or a history of blood glucose levels. A log book (FIG. 4-D) allows the patient to access and modify records of medication, symptoms/events, lab tests, treatment plans, diets, and appointment and checkup schedules. A mail center (FIG. 4-E) is used by the patient to download treatment directions from the health provider, to transfer log book contents to the service provider and/or the health provider, and to communicate by email with the health provider.

FIG. 5-A is a schematic depiction of a screen shot 90 of the Health Avatar™ application. The display comprises several sections: a body image section 100, a log book section 102, a blood glucose center section 104, a feedback section 106, and a mail center section 108. The patient accesses functions of the application by clicking on corresponding display sections or subsections.

The functions of the log book module become accessible if the patient clicks on log book section 102, as illustrated in FIG. 5-B. A similar display (not shown) is generated if the patient clicks on blood glucose center section 104. FIG. 5-C illustrates the display after the patient accesses the "Display Blood Glucose Level" (see FIG. 4-C) subfunction of the blood glucose center. Feedback section 106 enables the patient to record information about his or her health habits.

Body image 100 comprises subsections corresponding to the patient's organs and/or body parts. If a particular body part of the patient requires attention or care, the corresponding subsection of body image 100 is highlighted. FIG. 5-D depicts the application display if the diabetes patient neglects care of his or her feet. A display subsection corresponding to the patient's feet blinks, and the patient is prompted to make an appointment with a care provider.

The overall appearance of body image section 100 depends on the blood glucose level of the patient, and on the time since the last recording of the patient's blood glucose level. FIG.

5-E illustrates the application display if the patient fails to record or download his or her blood glucose levels according to a treatment plan.

FIG. 5-F schematically depicts the application display if the patient clicks on a subsection of body image 100 corresponding to the patient's heart. The patient can request general information about the heart in diabetes patients, about the current and historical conditions of his or her heart, and about other patients approaches to the hearts' care.

It will be clear to one skilled in the art that the above embodiment may be altered in many ways without departing from the scope of the invention. For example, many relative placements of the aggregation, processing, and display means may be suitable in a system of the present invention. In particular, the data aggregation means may be in communication with the processing means over a remote network. Suitable parameters, data sets, and processing functions can be readily determined by the skilled artisan for various applications. Systems and methods of the present invention are suitable for the management of any chronic disease or condition requiring regular medical attention and patient compliance with a treatment plan, including diabetes, asthma, AIDS, heart and cardiovascular disease, weight control programs, mental health conditions, attention deficit disorder, smoking, and substance abuse. Many display and patient input implementations, including non-HTML-based implementations, can be suitable for use with the present invention. Accordingly, the scope of the invention should be determined by the following claims and their legal equivalents.

The invention claimed is:

1. A method of displaying a personalized image representing an individual, comprising the steps of:
   (A) generating a health model of said individual using a computer, as a function of a data set selected from a log of data comprising one or more compliance questions relating to medication data, symptoms, events, treatment plans, lab tests, diets, appointment schedule, and checkup schedule;
   (B) the computer generating said personalized customized image based on said health model, said personalized image corresponding to at least one body part of said individual and at least one icon related to health information of said individual, wherein (i) said at least one icon appears and highlights said at least one body part when the body part corresponding to a portion of said personalized image has information to be displayed and (ii) said personalized image displays one or more conditions for one of said body parts in response to simulating hypothetical health care decisions proposed by a health care professional; and
   (C) displaying said personalized image on a display connected to the computer.

2. The method according to claim 1, wherein said personalized image further defines a feedback mechanism comprising a plurality of buttons corresponding to a plurality of behaviors of said individual.

3. The method according to claim 1, further comprising the step of:
   generating a pop-up window on said display in response to a user selection of said icon.

4. The method according to claim 3, wherein said icon comprises a log book icon.

5. The method according to claim 4, wherein said pop-up window associated with said log book icon comprises one or more buttons corresponding to one or more of (i) medication, (ii) events, (iii) lab tests, (iv) appointments and (v) checkup schedules.

6. The method according to claim 3, wherein said icon comprises one or more parameter icons.

7. The method according to claim 6, wherein said parameter icons correspond to one or more of (i) a blood glucose level, (ii) a respiratory flow, (iii) a blood pressure, (iv) a cholesterol level, (v) a patient weight, (vi) a T-cell count, (vii) a frequency of episodes, (viii) a compliance with treatment, (ix) a compliance with monitoring and (x) one or more body part conditions.

8. The method according to claim 3, wherein said icon comprises a mail icon.

9. The method according to claim 8, wherein said pop-up window corresponding to said mail icon contains one or more buttons corresponding to one or more of (i) sending email, (ii) receiving email, (iii) downloading treatment directions and (iv) transferring a log book to a service provider.

10. The method according to claim 3, wherein said pop-up window illustrates a portion of said data set in a graphical form.

11. The method according to claim 1, wherein said personalized image comprises a plurality of appearances illustrating a plurality of conditions of said individual based on said health model.

12. The method according to claim 1, wherein said personalized image further defines one or more highlighted regions corresponding to the at least one body part.

13. The method according to claim 12, wherein said personalized image further defines one or more pop-up windows associated with said highlighted regions.

14. The method according to claim 13, wherein each of said pop-up windows comprises a plurality of user selectable buttons, each of said buttons corresponding to a particular aspect of said health information.

15. The method according to claim 1, wherein said personalized image comprises one or more of (i) a schematic figure representation, (ii) a reproduction of an appearance of said individual, (iii) a representation of a cartoon, (iv) a representation of a fictional character and (v) a representation of a character in a field of interest of said individual.

16. A system comprising:
   a processor configured to (i) generate a health model of an individual using a computer as a function of a data set selected from a log of data comprising one or more of medication data, symptoms, events, treatment plans, lab tests, diets, appointment schedule, and checkup schedule and (ii) generate an image personalized based on said health model, said personalized image corresponding to at least one body part of said individual and at least one icon related to health information of said individual, wherein (i) said at least one icon appears and highlights said at least one body part when the body part corresponding to a portion of said personalized image has information to be displayed and (ii) said personalized image displays one or more conditions for one of said body parts in response to simulating hypothetical health decisions proposed by a health care professional; and
   a display configured to present said personalized image.

17. The system according to claim 16, further comprising an aggregator configured to generate said data set.

18. The system according to claim 17, wherein said aggregator generates said data set based on one or more of (i) customization data of said display, (ii) medical records, (iii) formularies, (iv) standards of care, (v) prescribed treatment, (vi) a health profile and (vii) simulation data.

19. The system according to claim 18, wherein said display is remotely located from said aggregator.

* * * * *